United States Patent
Barthe

(10) Patent No.: US 10,048,101 B2
(45) Date of Patent: Aug. 14, 2018

(54) LIQUID-FILLED ACOUSTIC PROBE SYSTEM WITH PRESERVOIR AND LOSS DETECTION MEANS

(71) Applicant: Ardent Sound, Inc., Mesa, AZ (US)

(72) Inventor: Peter G. Barthe, Phoenix, AZ (US)

(73) Assignee: ARDENT SOUND, INC., Mesa, AZ (US)

( * ) Notice: Subject to any disclaimer, the term of this patent is extended or adjusted under 35 U.S.C. 154(b) by 514 days.

(21) Appl. No.: 14/777,380

(22) PCT Filed: Mar. 17, 2014

(86) PCT No.: PCT/US2014/030779
§ 371 (c)(1),
(2) Date: Sep. 15, 2015

(87) PCT Pub. No.: WO2014/145926
PCT Pub. Date: Sep. 18, 2014

(65) Prior Publication Data
US 2016/0033310 A1    Feb. 4, 2016

Related U.S. Application Data

(60) Provisional application No. 61/800,609, filed on Mar. 15, 2013.

(51) Int. Cl.
   *G01D 21/00*    (2006.01)
   *A61N 7/00*    (2006.01)
   *A61B 17/225*    (2006.01)

(52) U.S. Cl.
   CPC .............. *G01D 21/00* (2013.01); *A61N 7/00* (2013.01); *A61B 2017/2253* (2013.01)

(58) Field of Classification Search
   CPC ... A61N 7/00; A61B 2017/2253; G01D 21/00
   See application file for complete search history.

(56) References Cited

U.S. PATENT DOCUMENTS

| | | | |
|---|---|---|---|
| 2002/0052550 A1 | 5/2002 | Madsen et al. | |
| 2009/0299175 A1 | 12/2009 | Bernstein et al. | |
| 2010/0063422 A1 | 3/2010 | Hynynen et al. | |
| 2011/0264012 A1 | 10/2011 | Lautzenhiser et al. | |
| 2016/0033310 A1* | 2/2016 | Barthe ................ | A61N 7/00 367/13 |

FOREIGN PATENT DOCUMENTS

| | | | | |
|---|---|---|---|---|
| WO | 2008-0249232 A2 | 2/2008 | | |
| WO | WO-2014145926 A2 * | 9/2014 | ............... | A61N 7/00 |

OTHER PUBLICATIONS

The International Search Report dated Sep. 1, 2014 for International Application No. PCT/US2014/030779.

* cited by examiner

*Primary Examiner* — Daniel Pihulic
(74) *Attorney, Agent, or Firm* — Quarles & Brady, LLP

(57) ABSTRACT

An acoustic system can include a liquid-filled coupling component comprising an acoustic coupling fluid and a housing encasing the coupling fluid; a fluid reservoir comprising an amount of the coupling fluid; a path in fluid communication between the coupling component and the fluid reservoir; and a bubble detector coupled to the path and configured to monitor the coupling fluid in the path.

20 Claims, 2 Drawing Sheets

LIQUID-FILLED ACOUSTIC PROBE SYSTEM WITH PRESERVOIR AND LOSS DETECTION MEANS

CROSS-REFERENCE TO RELATED APPLICATIONS

This application represents the national stage entry of PCT International Application No. PCT/US2014/030779 filed on Mar. 17, 2014 and claims priority to and the benefit of U.S. Provisional Patent Application Ser. No. 61/800,609, filed Mar. 15, 2013, the entire contents of which are incorporated by reference herein.

BACKGROUND

Liquid-filled acoustic probes can be adversely impacted by fluid loss, air bubbles, volumetric shrinkage, and/or loss of performance or failure. What is needed are systems and methods of mitigating fluid loss, as well as, taking action, when necessary, to maintain safety and treatment efficacy.

SUMMARY

In some embodiments, an acoustic system can include a liquid-filled coupling component comprising an acoustic coupling fluid and a housing encasing the coupling fluid; a fluid reservoir comprising an amount of the coupling fluid; a path in fluid communication between the coupling component and the fluid reservoir; and a bubble detector coupled to the path and configured to monitor the coupling fluid in the path.

Some embodiments provide methods of monitoring a liquid-filled coupling component. An exemplary method can include the steps of providing an acoustic probe comprising an amount of a coupling fluid distributed in a liquid-filled coupling component, a fluid reservoir, and a path in fluid communication between the coupling component and the reservoir; operating the probe to emit acoustic energy through the coupling component; monitoring an amount of air in at least one of the fluid reservoir and the path; determining the amount of air and comparing the amount of air to a threshold; and stopping the emit acoustic energy if the threshold is reached.

DRAWINGS

Figure 1:
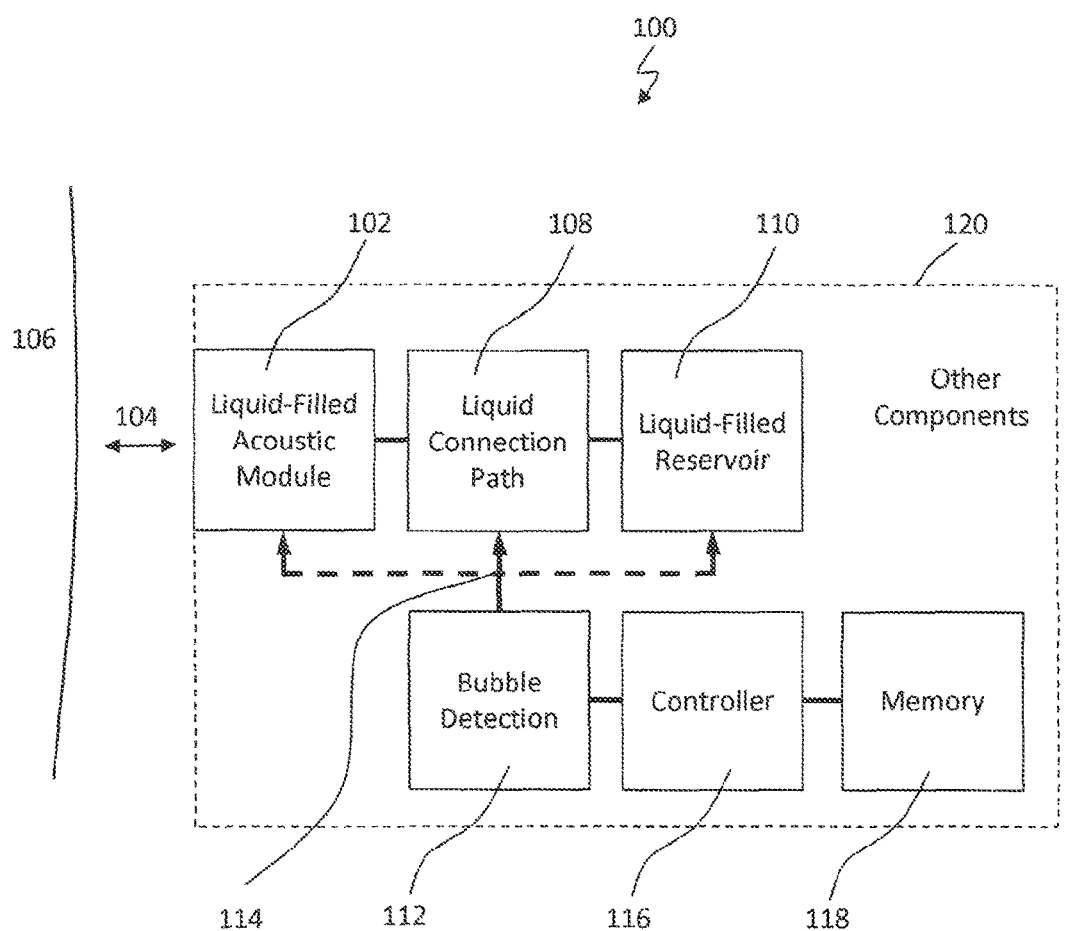
Figure 2:
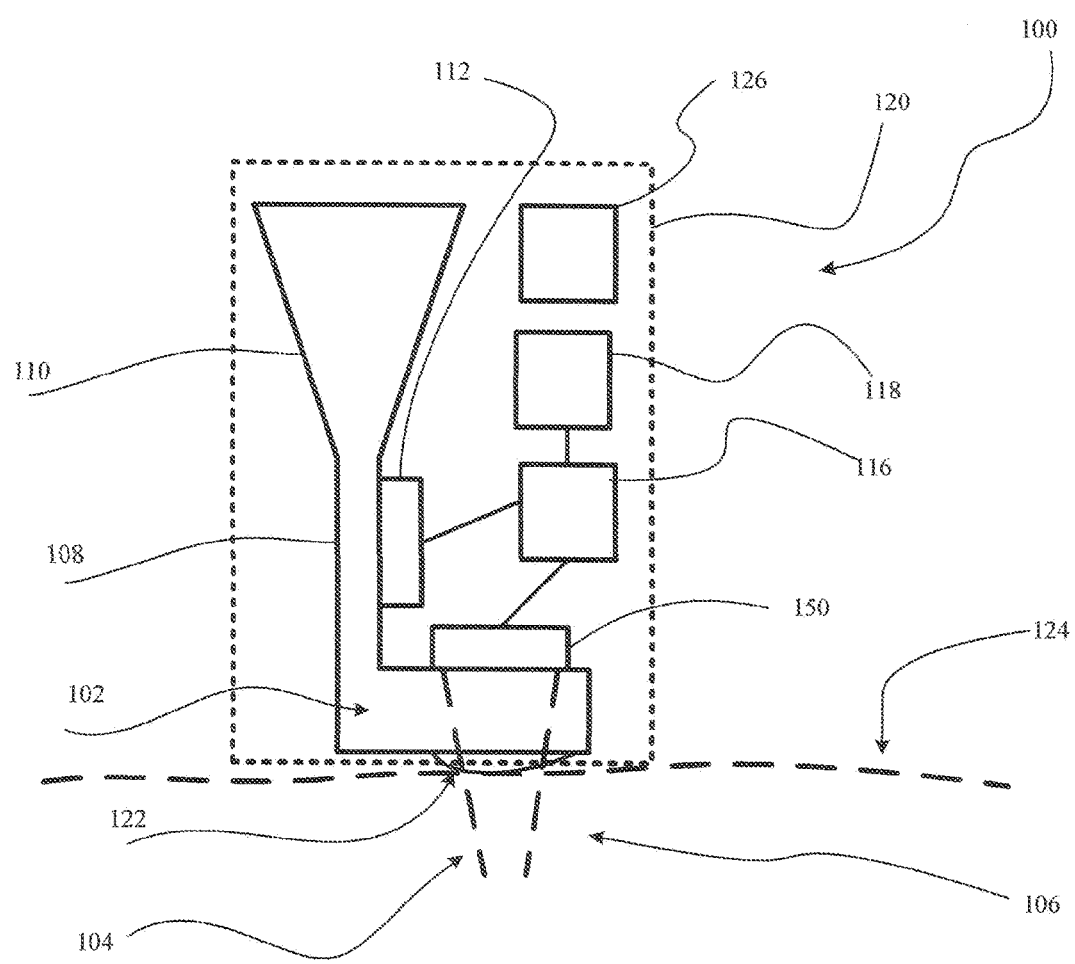

The present disclosure will become more fully understood from the specification and the accompanying drawing, wherein:

FIG. 1 is a block diagram illustrating an exemplary system, in accordance with some embodiments of the present invention; and FIG. 2 is a diagram illustrating an exemplary system, in accordance watt some embodiments of the present invention.

The drawings described herein are for illustrative purposes only of selected embodiments and not all possible implementations, and are not intended to limit the scope of any of the exemplary embodiments disclosed herein or any equivalents thereof. It is understood that the drawings are not drawn to scale. For purposes of clarity, the same reference numbers will be used in the drawings to identify similar elements.

DESCRIPTION

The following description is merely exemplary in nature and is in no way intended to limit the exemplary embodiments, their application, or uses. Various embodiments of the present invention may be practiced in any number of any medical or non-medical contexts, which may be directed to a method and/or a system for acoustic tissue treatment. For example, various aspects the embodiments may be suitably applied to cosmetic applications, such as, for example, cosmetic enhancement of skin and/or various subcutaneous tissue layers and/or fat reduction.

For example, a cosmetic enhancement can be a procedure, but not limited to procedures. Which are used to improve or change the appearance of a nose, eyes, eyebrows and/or other facial features, or to improve or change the appearance and/or the texture and/or the elasticity of skip, or to improve or change the appearance of a mark or scar on a skin surface, or to improve or change the appearance and/or the content of fat near a skin surface, or the targeting of a gland to improve or change the appearance a portion of the body. Some examples of a cosmetic enhancement can include a procedure, but not limited to procedures, which are used to improve an appearance of cellulite and/or reduce subcutaneous fat. In some embodiments, methods of cosmetic enhancement can increase elasticity of skin by thinning a dermis layer, thereby rejuvenating a portion of skin. In some embodiments, methods of cosmetic enhancement can stimulate initiation of internal body resources for the purpose of repairing an injury and/or cell defects. Some embodiments provide an acoustic treatment system configured for temporarily or permanently affecting tissue or its physiology. In at least one embodiment, cosmetic enhancement is an acoustic treatment, which is a non-surgical and non-invasive procedure.

In some embodiments, an acoustic system can comprise, a liquid-filled coupling component comprising an acoustic coupling fluid and a housing encasing the coupling fluid; a fluid reservoir comprising an amount of the coupling fluid; a path in fluid communication between the coupling component and the fluid reservoir; and a bubble detector coupled to the path and configured to monitor the coupling fluid in the path.

The system according can comprise a controller in communication with the bubble detector and configured to receive a signal from the bubble detector. The signal can be a measurement, such as, for example, a measurement of an amount of air in the path. The controller can determine whether to shut off the acoustic system based on the amount of air in the path. In some embodiments, the bubble detector comprises an algorithm configured to determine an amount of air in the path based on the monitoring the coupling fluid in the path and to provide a shut-off signal to the controller if the amount of air in the path is above a threshold level.

In another example, the signal can be a measurement of an amount of time that air is detected in the path. The controller can determine whether to shut off the acoustic system based on the amount of time that air is detected in the path. In some embodiments, the bubble detector comprises an algorithm configured to determine an amount of time that air is detected in the path based on the monitoring the coupling fluid in the path and to provide a shut-off signal to the controller if the amount of time that air is detected in the path is above a threshold level.

The system can comprise a clock configured to provide a shut off signal when an expiration date of the liquid-filled coupling component has been reached. The system can include memory configured to retain and communicate the expiration date. The liquid-filled coupling component can include a housing encasing the fluid and configured to prevent seepage of the fluid through the housing.

The acoustic system can comprise a positive pressure within the liquid-filled coupling component, the fluid path, and the reservoir. The acoustic system can comprise an acoustic transducer coupled to the liquid-filled coupling component and configured to emit acoustic energy through the liquid-filled coupling component and into a region of interest, which is acoustically coupled to the liquid-filled coupling component. The acoustic membrane can be positioned in a path of the acoustic energy and in contact with a surface above a region of interest. The positive pressure can be configured to push the acoustic membrane against the surface.

The acoustic system can comprise a negative pressure within the liquid-filled coupling component, the fluid path, and the reservoir. The reservoir can be a collapsible housing configured to shrink a reservoir volume under the negative pressure as the amount of fluid decreases. The system can include a sensor configured to detect an empty position of the collapsible housing and provide a shut off signal to the controller when the empty position is reached.

The system can include an acoustic transducer coupled to the liquid-filled coupling component and configured to emit acoustic energy through the liquid-filled coupling component and into a region of interest, which is acoustically coupled to the liquid-filled coupling component. The acoustic transducer can be configured to receive a reflected acoustic energy. The acoustic transducer can be configured to treat a region of interest. The acoustic transducer can be configured to image a region of interest. The acoustic transducer can be configured to treat and image a region of interest. The system can be configured to move a bubble in the liquid-filled coupling component up into the path and/or the reservoir when the system is put into a treatment mode.

Some embodiments provide a method of monitoring a liquid-filled coupling component. The method can include the steps of providing an acoustic probe comprising an amount of a coupling fluid distributed in a liquid-filled coupling component, a fluid reservoir, and a path in fluid communication between the coupling component and the reservoir; operating the probe to emit acoustic energy through the coupling component; monitoring an amount of air in at least one of the fluid reservoir and the path; determining the amount of air and comparing the amount of air to a threshold; and stopping the emit acoustic energy if the threshold is reached.

The method can include monitoring an amount of time that an amount of air in at least one of the fluid reservoir and the path; determining if the amount of air is above a time threshold; and stopping the emit acoustic energy if the time threshold is reached.

Some embodiments provide a method of monitoring a liquid-filled coupling component. The method can include the steps of: providing an acoustic probe comprising an amount of a coupling fluid distributed in a liquid-filled coupling component, a fluid reservoir, and a path in fluid communication between the coupling component and the reservoir; operating the probe to emit acoustic energy through the coupling component; monitoring an amount of time that an amount of air in at least one of the fluid reservoir and the path; determining if the amount of air is above a threshold; and stopping the emit acoustic energy if the threshold is reached.

The method can include monitoring an amount of air in at least one of the fluid reservoir and the path; determining the amount of air and comparing the amount of air to an air threshold; and stopping the emit acoustic energy if the air threshold is reached.

The methods can include refilling the fluid reservoir with the coupling fluid and resetting the probe. The methods can include providing an alarm if the threshold is reached. The methods can include monitoring a clock configured to identify an expiration date; and stopping the emit acoustic energy if the expiration date is reached. The methods can include sensing if the liquid-filled coupling component is coupled to region of interest and stopping the emit acoustic energy if the liquid-filled coupling component is not coupled to region of interest.

The methods can include providing a positive pressure within the liquid-filled coupling component, the fluid reservoir, and the path. The methods can include contacting an acoustic membrane with a surface above a region of interest, wherein the liquid-filled component comprises the acoustic membrane in a path of the acoustic energy. The methods can include providing a positive pressure within the liquid-filled coupling component, the fluid reservoir, and the path; and pushing the acoustic membrane against the surface.

The method can include providing a negative pressure within the liquid-filled coupling component, the fluid reservoir, and the path. The method can include collapsing the fluid reservoir to shrink a reservoir volume under the negative pressure as the amount of fluid decreases. The methods can include detecting an empty position of fluid reservoir; and stopping the emit acoustic energy if the empty position is reached.

The methods can include engaging the probe into a treatment mode on a surface of a region of interest; and moving a bubble in the liquid-filled coupling component up into the fluid reservoir and/or the path. The methods can include providing active flow control to move the acoustic fluid from the fluid reservoir to liquid-filled coupling component.

Referring to FIGS. 1 and 2, an acoustic system 100 comprises a liquid-filled acoustic module 102 which is configured to propagate acoustic energy 104 to and/or from a region of interest 106 via an acoustic couplant. The acoustic system 100 can be contained within a device housing 120. The acoustic system 100 can a controller 116, which can be in communication with a bubble detection 112 and an acoustic transducer 150. Liquid-filled acoustic module 102 is enclosed by a housing, which is typically made from a material that has a small but non-zero fluid permeation through, and subsequent evaporation from, the external surface of housing. This fluid loss from such fluid permeation, if left unchecked, will eventually reduce performance of acoustic system 100, since acoustic energy 104 cannot propagate through the air voids, or bubbles, created by loss of fluid.

Various effects may occur at the liquid-filled acoustic module 102 depending on the rate of gas permeation versus fluid permeation of the acoustic system 100. Air molecule ingress can occur and fill, the void left by fluid loss (creating one or more bubbles). Shrinkage of the liquid-filled acoustic module 102 may occur via volumetric fluid loss, creating a "suck-in" phenomenon, such as suck-in of a thin acoustic membrane 122 typically disposed as part of the liquid-filled, acoustic module housing 120. In addition, biometric loss can also affect a shelf life of the liquid-filled acoustic module 102. The liquid-filled acoustic module 102 can include a housing encasing the coupling fluid and configured to prevent seepage of the fluid or fluid permeation through the housing.

By providing a liquid-filled reservoir 110, with a liquid connection path 108 to the liquid-filled acoustic module 102, the loss of fluid in liquid-filled acoustic module 102, can be compensated for, thereby eliminating bubbles or suck-in of liquid-filled acoustic module 102. The bubble detection 112 can be coupled to liquid connection path 108. In some embodiments, the bubble detection 142 can be coupled to any of the liquid-filled acoustic module 102, the liquid-filled connection path 108, and the liquid-filled reservoir 110. In one example, the liquid-filled connection path 108 and the liquid-filled reservoir 110 can be integrated into a single unit, and the bubble detection 112 can be coupled to the single unit. In some aspects, the liquid-filled reservoir 110 can mechanically or functionally merged with liquid connection path 108 and/or in any combination with liquid-filled acoustic module 102.

In accordance with various embodiments, n least one of liquid connection path 108, liquid-filled acoustic module 102, and/or liquid-filled reservoir are monitored 114 for bubbles or simply loss of fluid via bubble detection 112, Bubble detection 112 can be accomplished by means of any electro-acoustic, electro-mechanical, mechanical, electrical, electro-optical or other means, such as through-transmission or reflective sensing, electric-acoustic impedance sensing, stiffness or compliance sensing, capacitive sensing, visual, and other means.

The bubble can be detected white passing through liquid connection path 108. Detection of bubble or fluid loss via, monitoring 114 can be binary or proportional to size of bubble of fluid loss.

A controller 116 can be in control of and/or communication with bubble detection 112 writes to a non-volatile or volatile memory 118 that a bubble or fluid loss has been detected. The controller 116 can disable the acoustic transmission 104 from liquid-filled acoustic module 102 when bubble or liquid loss are above a certain threshold, which can adversely impact safety and/or efficacy of acoustic system 100.

The acoustic system 100 can comprise a controller in communication with the bubble detector 112 and configured to receive a signal from the bubble detector 112. The signal can be a measurement, such as, for example, a measurement of an amount of air in the liquid connection path 108 or the liquid reservoir 110. The controller can determine whether to shut off the acoustic system 100 based on the amount of air in the liquid connection path 108 or the liquid reservoir 110. In some embodiments, the bubble detector 116 can comprise an algorithm configured to determine an amount of air in the liquid connection path 108 or the liquid reservoir 110 based on the monitoring the coupling fluid in the liquid connection path 108 or the liquid reservoir 110 and to provide a shut-off signal to the controller 116 if the amount of air in the liquid connection path 108 or the liquid reservoir 110 is above a threshold level.

In another example, the signal can be a measurement of an amount of time that air is detected in the liquid connection path 108 or the liquid reservoir 110. The controller 116 can determine whether to shut off the acoustic system 100 based on the amount of time that air is detected in the liquid connection path 108 or the liquid reservoir 110. In some embodiments, the bubble detector 112 comprises an algorithm configured to determine an amount of time that air is detected in the liquid connection path 108 or the liquid reservoir 110 based on the monitoring the coupling fluid in the liquid connection path 108 or the liquid reservoir 110 and to provide a shut-off signal to the controller 116 if the amount of time that air is detected in the liquid connection path 108 or the liquid reservoir 110 is above a threshold level.

The acoustic system 100 can comprise a clock configured to provide a shut off signal when an expiration date of the liquid-filled acoustic module 102 has been reached. The acoustic system 100 can include memory configured to retain and communicate the expiration date.

For example, gross fluid leaks, such as those occurring by damage to or failure of acoustic system 100 are detected by bubble detection 112, and controller 116 disables the acoustic transmission 104 from liquid-filled acoustic module 102, when such leaks are above a certain threshold, which can adversely impact safety and/or efficacy of acoustic system 100.

The rate of gas ingress versus liquid loss in the liquid-filled reservoir 110 can be controlled via selection of materials such that, as fluid loss occurs in the liquid-filled acoustic module 102, the liquid-filled reservoir 110 passively collapses or shrinks in volume over time and loses its volume of fluid through the liquid-connection path 108 to the liquid-filled acoustic module 102. One or more sensors can be included to detect an empty position of the liquid-filled reservoir 110, such as, a certain point of the passively collapsing, and provide a shut off signal to the controller when the empty position is reached.

In various embodiments the liquid-filled reservoir 110 is pressurized, such as via a spring or other mechanical stress, such that as fluid loss occurs in the liquid-filled acoustic module 102 the liquid-filled reservoir 110 provides a replacement volume of fluid through the liquid-connection path 108.

In various embodiments, excess pressure in the liquid of acoustic system 100 created by a pressurized liquid-filled reservoir 110 creates a harrier to gas ingress into the liquid-filled acoustic module 102. This is because external air is at atmospheric or ambient pressure whereas internal gas molecules entrained in the liquid are at higher pressure. The excess pressure in the liquid of acoustic system 100 can be created by a pressurized liquid-filled reservoir 110 can prevent suck-in or collapse of housing and/or acoustic membrane 122 of liquid-filled acoustic module 102. The excess pressure in the liquid of acoustic system 100 created by a pressurized liquid-filled reservoir 110 can prevent cavitation within the liquid-filled acoustic module 102. In addition, the pressurized liquid-filled reservoir 110 can improve coupling of the acoustic membrane 112 and a surface 124 of the region of interest 106.

In various embodiments the total rate of fluid loss and total volumes of the liquid-filled acoustic module 102, liquid-connection path 108, and liquid-filled reservoir 110 are configured such that over a certain time period, such as the lifetime of the device, that the performance of acoustic system 100 is not adversely impacted, such that no bubbles are present or that an acceptable fluid loss is present.

In various embodiments the total rate of fluid loss and total volumes of the liquid-filled acoustic module 102, liquid-connection path 108, and liquid-filled reservoir 110 are configured such that after a certain time period a known fluid loss is present, whereby such known fluid loss trips monitoring 114 threshold and invokes controller 116 to disable acoustic system 100.

In various embodiments liquid connection path 108 and liquid-filled reservoir 110 allow adequate amount of fluid to be supplied to liquid-filled acoustic module 102 over lifetime of device without re-filling, which in various embodiments is further beneficial if liquid-filled acoustic module 102 has small volume and/or miniature size.

In various embodiments the total rate of fluid loss is known. Using a shelf life of the acoustic system 100, a total fluid loss can be estimated. Accordingly total volumes of the liquid-filled acoustic module 102, liquid-connection path 108, and liquid-filled reservoir 110 are greater than the total fluid loss, as estimated. In some embodiments, the liquid-filled reservoir 110 is sized to hold the total fluid loss, as estimated. At approximately the time expiration date of the shelf life of the acoustic system 100, the total fluid loss, as estimated, has caused the liquid-filled acoustic module to collapse. Once the total fluid loss, as estimated has left the liquid-filled reservoir 110, the collapsing liquid-filled reservoir 110 triggers a sensor, which is coupled to the controller 116. After the sensor has been triggered and a signal sent to the controller 116, the acoustic system is turned off by the controller 116. A message regarding the need to replace the liquid-filled acoustic module 102 can be communicated to a user by the acoustic system 100.

In various embodiments liquid-filled reservoir 110 is an enclosure impervious to air molecules such that as liquid-filled acoustic module 102 loses fluid the liquid-filled reservoir 110 crumples, collapses, or shrinks while it supplies its own fluid to the liquid-filled acoustic module 102 via small volume and/or miniature size. In various embodiments the liquid, such as, a coupling fluid, can be wholly or in part replaced by a gel or low viscosity gel and in air-coupled applications a gas.

The acoustic system 100 can include an acoustic transducer 150 coupled to the liquid-filled acoustic module 102 and configured to emit acoustic energy 104 through the liquid-filled acoustic module 102 and into a region of interest 106, Which is acoustically coupled to the liquid-filled acoustic module 102. The acoustic transducer 150 can be configured to receive a reflected acoustic energy. The acoustic transducer 150 can be configured to treat a region of interest 106. The acoustic transducer 150 can be configured to image a region of interest 150, The acoustic transducer 150 can be configured to treat and image a region of interest 106. The acoustic system 100 can be configured to move a bubble in the liquid-filled acoustic module 102 up into the liquid connection path 108 and/or the liquid-filled reservoir 110 when the acoustic system 100 is put into a treatment mode.

In some applications, the region of interest 106 can be subcutaneous tissue below a skin surface 124. The acoustic system 100 can be employed in cosmetic enhancement of skin and/or various subcutaneous tissue layers and/or fat reduction. The acoustic system 100 can be configured for temporarily or permanently affecting the subcutaneous tissue or its physiology. The acoustic system 100, and its methods of us, can be configured for cosmetic enhancement using an acoustic treatment, which is a non-surgical and non-invasive procedure.

As used herein, the terms "comprise", "comprises", "comprising", "having", "including", "includes" or any variation thereof, are intended to reference a non-exclusive inclusion, such that a process, method, device, system, composition or apparatus that comprises a list of elements does not include only those elements recited, but may also include other elements not expressly listed or inherent to such process, method, device, system, composition or apparatus.

As used herein, the phrase "at least one of A, B, and C" can be construed to mean a logical (A or B or C), using a non-exclusive logical "or," however, can be contrasted to mean (A, B, and C), in addition, can be construed to mean (A and B) or (A and C) or (B and C). As used herein, the phrase "A, B and/or C" should be construed to mean (A, B, and C) or alternatively (A or B or C), using a non-exclusive logical "or."

It should be understood that steps within a method may be executed in different order without altering the principles of the present disclosure. The some embodiments may be described herein in terms of various functional components and processing steps. It should be appreciated that such components and steps may be realized by any number of hardware components configured to perform the specified functions.

The present invention has been described above with reference to various exemplary embodiments and examples, which are not intended to be limiting in describing the full scope of systems and methods of this invention. However, those skilled in the art will recognize that equivalent changes, modifications and variations of the embodiments, materials, systems, and methods may be made within the scope of the present invention, with substantially similar results, and are intended to be included within the scope of the present invention, as set forth in the following claims.

The invention claimed is:

1. An acoustic system comprising:
   a liquid-filled coupling module comprising an acoustic coupling fluid and a housing encasing the coupling fluid;
   a fluid reservoir comprising an amount of the acoustic coupling fluid;
   a path in fluid communication between the liquid-filled coupling module component and the fluid reservoir; and
   a bubble detector coupled to the path and configured to monitor the coupling fluid in the path.

2. The acoustic system according to claim 1, further comprising a controller in communication with the bubble detector and configured to receive a signal from the bubble detector.

3. The acoustic system according to claim 2, wherein the signal comprises a measurement of an amount of air in the path.

4. The acoustic system according to claim 3, wherein the controller determines whether to shut off the acoustic system based on the amount of air in the path.

5. The acoustic system according to claim 2, wherein the bubble detector or the controller comprises an algorithm configured to determine an amount of air in the path based on the monitoring the coupling fluid in the path and to provide a shut-off signal to the controller if the amount of air in the path is above a threshold level.

6. The acoustic system according to claim 2, wherein the signal comprises a measurement of an amount of time that air is detected in the path.

7. The acoustic system according to 6, wherein the controller determines whether to shut off the acoustic system based on the amount of time that air is detected in the path.

8. The acoustic system according to claim 2, wherein the bubble detector comprises an algorithm configured to determine an amount of time that air is detected in the path based on the monitoring the acoustic coupling fluid in the path and to provide a shut-off signal to the controller if the amount of time that air is detected in the path is above a threshold level.

9. The acoustic system according to claim 1, further comprising a negative pressure within the liquid-filled coupling component module, the fluid path, and the reservoir.

10. The acoustic system according to claim 9, wherein the reservoir comprises a collapsible housing configured to shrink a reservoir volume under the negative pressure as the amount of fluid decreases.

11. The acoustic system according to claim 10, further comprising a sensor configured to detect an empty position of the collapsible housing and provide a shut off signal to the controller when the empty position is reached.

12. The acoustic system according to claim 2, further comprising a clock configured to provide a shut off signal when an expiration date of the liquid-filled coupling component has been reached.

13. A method of monitoring a liquid-filled coupling module, the method comprising:
   providing an acoustic probe comprising an amount of a coupling fluid distributed in a liquid-filled coupling module, a fluid reservoir, and a path in fluid communication between the coupling component liquid-filled coupling module and the fluid reservoir;
   operating emitting acoustic energy from the probe to emit acoustic energy through the liquid-filled coupling module;
   monitoring an amount of air or the amount of the coupling fluid in at least one of the liquid-filled coupling module, the fluid reservoir, the path, or a combination thereof;
   determining the amount of air and comparing the amount of air to a threshold; and
   in response to the monitored amount of air or amount of the coupling fluid in the liquid-filled coupling module, the fluid reservoir, the path, or a combination thereof being above or below a threshold, adjusting a fluid pressure in the liquid-filled coupling module, the fluid reservoir, the path, or a combination thereof or stopping the emitting acoustic energy if the threshold is reached.

14. The method according to claim 13, the method further comprising;
   monitoring a clock configured to identify determine if an expiration date of the liquid-filled coupling module has been reached; and
   stopping the emitting acoustic energy if the monitoring the clock step determines that the expiration date has been reached.

15. The method according to claim 13, the method further comprising:
   sensing a coupling between the liquid-filled coupling module is coupled to and a region of interest; and
   in response to the sensed coupling being interrupted, increasing the fluid pressure in the liquid-filled coupling module, the fluid reservoir, the path, or a combination thereof or stopping the emitting acoustic energy if the liquid-filled coupling module is not coupled to region of interest.

16. The method according to claim 13, the method further comprising:
   monitoring an amount of time that the amount of air in at least one of the fluid reservoir and the path;
   determining if the amount of air is above a time threshold; and
   stopping the emitting acoustic energy if the amount of time exceeds a time threshold is reached.

17. A method of monitoring a liquid-filled coupling module, the method comprising:
   providing an acoustic probe comprising an amount of a coupling fluid distributed in a liquid-filled coupling module, a fluid reservoir, and a path in fluid communication between the coupling component liquid-filled coupling module and the fluid reservoir;
   operating emitting acoustic energy from the probe to emit acoustic energy through the liquid-filled coupling module;
   monitoring the amount of time that an amount of air the coupling fluid in at least one of the liquid-filled coupling module, the fluid reservoir, the path, or a combination thereof;
   determining if the amount of air is above a threshold; and
   in response to the monitoring determining that the amount of the coupling fluid is decreased, introducing a positive pressure to the liquid-filled coupling module, the fluid reservoir, the path, or a combination thereof or stopping the emitting acoustic energy if the threshold is reached.

18. The method according to claim 17, the method further comprising:
   monitoring an amount of air in at least one of the fluid reservoir and the path;
   determining the amount of air and comparing the amount of air to an air threshold; and
   stopping the emit acoustic energy if the air threshold is reached
   sensing a coupling between the liquid-filled coupling medium and a region of interest; and
   stopping the emitting acoustic energy if the coupling between the liquid-filled coupling module and the region of interest is interrupted.

19. The method according to claim 17, the method further comprising:
   detecting an empty position of the fluid reservoir; and
   stopping the emitting acoustic energy if the empty position is reached.

20. The method according to claim 17, the method further comprising:
   engaging the probe into a treatment mode on a surface of a region of interest; and
   moving a bubble from the liquid-filled coupling module into the fluid reservoir and/or the path.

* * * * *

UNITED STATES PATENT AND TRADEMARK OFFICE
CERTIFICATE OF CORRECTION

PATENT NO. : 10,048,101 B2
APPLICATION NO. : 14/777380
DATED : August 14, 2018
INVENTOR(S) : Peter G. Barthe It is certified that error appears in the above-identified patent and that said Letters Patent is hereby corrected as shown below:

On the Title Page

Item (54), Title, Line 2, "PRESERVIOR" should be --RESERVOIR--.

In the Specification

Column 1, Line 53, "watt" should be --with--.

Column 2, Line 10, "procedures. Which" should be --procedures, which--.

Column 2, Line 13, "skip" should be --skin--.

Column 5, Line 14, "n least" should be --at least--.

Column 5, Line 25, "white" should be --while--.

Column 6, Line 32, "harrier" should be --barrier--.

Signed and Sealed this
Twelfth Day of February, 2019

Andrei Iancu
*Director of the United States Patent and Trademark Office*